United States Patent [19]

Dennis

[11] Patent Number: 5,352,673
[45] Date of Patent: * Oct. 4, 1994

[54] PRODRUGS

[76] Inventor: Edward A. Dennis, 1921 Hypatia Way, La Jolla, Calif. 92037-3322

[ * ] Notice: The portion of the term of this patent subsequent to May 3, 2011 has been disclaimed.

[21] Appl. No.: 712,968

[22] Filed: Jun. 10, 1991

Related U.S. Application Data

[63] Continuation of Ser. No. 713,116, Jun. 10, 1991, Pat. No. 5,308,766, and Ser. No. 399,799, Aug. 29, 1989, abandoned.

[51] Int. Cl.$^5$ .......................................... A61K 31/685
[52] U.S. Cl. .......................................... 514/78; 554/78; 554/79; 554/80; 554/81; 554/36; 554/42; 435/184
[58] Field of Search ............... 260/403; 538/727, 853, 538/861; 558/179, 180; 554/78, 79, 47, 48, 36, 42, 101, 106, 121; 514/78; 435/184

[56] References Cited

U.S. PATENT DOCUMENTS 4,847,376 7/1989 Neuman et al. ..................... 541/102

FOREIGN PATENT DOCUMENTS

| 3094389 | 3/1989 | Australia . |
| 10037583 | 10/1981 | European Pat. Off. . |
| 20271731 | 6/1988 | European Pat. Off. . |
| 20333167 | 9/1989 | European Pat. Off. . |

OTHER PUBLICATIONS

Gaetjens et al, Journal of the American Chemical Society, 42: 5328, 1960.
Cheng et al, Biochemical Pharmacology, vol. 36, #15, pp. 2429–2436, 1987.
Reynolds et al, Journal of the American Chemical Society, vol. 110, pp. 0772–0777 Rbeles, CCEN, 1983.
Edwards et al, Journal of the American Chemical Society vol. 112, #5, 1990, pp. 2042–2043.
Washburn, W. N., et al. J. Am. Chem. Soc. 112:2042 (1990).
Washburn, W. N., et al. J. Biol. Chem. 266:5042 (1991).
Reynolds, L. J., et al., Assay Strategies and Methods for Phospholipases In: Methods in Enzymology, vol. 197, ed. E. A. Dennis, publ. Harcourt, Brace, Jovanovich (1991).
Gaetjens, E., et al., J. Am. Chem. Soc. 82:5328 (1960).
Reynolds, L. J., J. Am. Chem. Soc. 110:5172 (1988).

*Primary Examiner*—Jose' G. Dees
*Assistant Examiner*—D. D. Carr
*Attorney, Agent, or Firm*—Jan P. Brunelle; Walter H. Dreger

[57] ABSTRACT

The present invention provides prodrugs that serve as useful therapeutics for various disease states and conditions mediated by underlying specific hydrolytic enzyme activity. The prodrugs hereof (additionally) impart a physiologically bioactive component thus providing prodrug compounds that are capable of imparting dual effect systemically.

25 Claims, No Drawings

PRODRUGS

The present invention is a continuing application of U.S. Ser. No. 07/713,116, filed Jun. 10, 1991, now U.S. Pat. No. 5,308,766 and U.S. Ser. No. 07/399,799, filed 29 Aug. 1989, now abandoned.

The application filed Aug, 29, 1989 is directed to novel hydrolyric enzyme inhibitors/inactivators and substrates functioning as suicide-inhibitory bifunctionally linked substrates (SIBLINKS) useful as 1) therapeutics for pathological disease states or conditions mediated by specific hydrolytic enzyme activity and 2) enzyme substrates for assays specific to hydrolytic enzyme activity. The continuing application of that earlier application, filed concurrently herewith, focuses on the function of the disclosed compounds as inhibitors/inactivators of said hydrolytic enzymes. That distinct use forms the basis of therapeutics and of methods of treatment using such therapeutics. That distinct aspect of the subject matter disclosed in the earlier application is characterized by the novel compounds useful for that embodiment as being physiologically acceptable, and in particular, that the leaving group disclosed, BX, or its component, B, be one that is physiologically acceptable. Further, the rate of leaving of the BX group is such that, together with the enzyme hydrolysis of moiety AX of said compounds, intramolecular cyclization of the functional residue attends consequent reactivity with the active site of the target hydrolytic enzyme such that it is inhibited/inactivated. That end point can be exploited clinically in the treatment of disease states or conditions that are manifest by the mediated activity of the hydrolytic enzyme.

The present application is directed to a specific subset of such therapeutics, that function as prodrugs.

FIELD OF INVENTION

The present invention in all of its aspects utilizes as a fundamental predicate a novel subset of a class of hydrolyric enzyme inhibitors (inactivators)/substrates and their use as prodrugs in the therapeutic treatment of pathological disease states or conditions mediated by specific hydrolytic enzyme activity. These inhibitors function as suicide-inhibitory bifunctionally linked substrates (SIBLINKS) and are characterized as an ensemble of three functional moieties: 1) one recognizable by (an) active site(s) of a given hydrolytic enzyme such that the enzyme functions hydrolytically when contacted with the inhibitor with attendant removal of that moiety, 2) leaving group that is physiologically acceptable and that itself is a physiologically bioactive moiety useful systemically and 3) a remainder moiety linking the first and second that assumes a cyclic configuration after removal of the first and second moieties that may attend its further reaction with the enzyme active site thus irreversibly inactivating or inhibiting bioactivity of the enzyme through covalent bond formation at said active site(s). IF the inactivating reaction does not take place, as it is not a prerequisite herein, the cyclic residue is otherwise physiologically removed. While, in preferred embodiments, benefits both of the enzyme inactivation and of the physiologically acceptable and bioactive moiety are clinically useful, in all events, availability of the physiologically acceptable and bioactive moiety is a predicate of the present invention.

The novel hydrolyric inhibitors/inactivators of the present invention thus create means for modulating hydrolytic enzyme activity in the control or treatment of various disease states or conditions in which such hydrolyric enzyme activity is implicated. Additionally, as the present compounds can be considered "prodrugs", they also provide physiologically bioactive properties by virtue of the therapeutic effect provided by the physiologically bioactive leaving group that is liberated in the mechanism attending the optional inactivation of the hydrolytic enzyme activity.

BACKGROUND OF INVENTION

Considerable background material can be taken from the appropriate section of the above cited earlier applications, and such subject matter is hereby expressly incorporated by reference.

The object of an invention disclosed in the earlier applications was to produce substances that can interfere with disease states or conditions via molecular interaction of specific hydrolytic enzyme activity on a suicidal inactivation or inhibitor mechanistic level. Based upon that research and study, using phospholipase $A_2$ as a model, the invention focused on the design of novel hydrolytic enzyme inhibitors (inactivators) functioning via recognition by the active site of such enzymes resulting in inhibition of enzyme functionality. Thus, the inhibitors invited functional suicide of the enzymatic activity.

SUMMARY OF THE INVENTION

Taken in its several aspects the present invention stems from the fundamental predicate based upon a novel class of hydrolytic enzyme inhibitors (inactivators) and substrates that function notably as prodrugs. These novel compounds function after recognition and processing by a specific hydrolytic enzyme, in preferred applications inhibiting said enzyme or inactivating said enzyme irreversibly. In the process mechanistically of optionally inhibiting or inactivating said enzyme, a functional moiety is generated that itself is physiologically bioactive thus imparting (additional) therapeutic effect. Preferred means thus form the basis of therapeutics having dual effect and of methods of treatment using such therapeutics. The present invention primarily provides a prodrug that serves as a delivery means of a physiologically acceptable, bioactive drug entity. The present invention further produces associated means germane to such clinically distinct treatment methods.

All of the foregoing aspects and all of their associated embodiments that will be represented as equivalents within the skill of the relevant art are also included within the ambit and/or interpretation of the present invention.

The novel prodrugs of the present invention may be represented by the following generic formula (I):

wherein

R is an oxygen atom or an imino group, each X independently is an oxygen atom, a sulfur atom or an imino group, A is an enzyme-specific moiety that facilitates recognition by and hydrolysis of the bond linking AX with C(0)Y by a target hydrolyric enzyme, B is a component of a physiologically acceptable leaving group BX that together with the enzyme hydrolysis of AX, attends intramolecular cyclization of the functional residue, and is itself physiologically bioactive, Y is a linker that provides a steric environment facilitating intramolecular cyclization of said functional residue with optional consequent reactivity with the active site of said target hydrolyric enzyme.

More specifically, the novel prodrugs of the present invention, as represented above by formula I, can be represented as a preferred sub-grouping of compounds of the following formula (II);

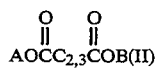
$$AOCC_{2,3}COB(II)$$

wherein each of A and B is as defined above and $C_{2,3}$ represents a linker species having at least two or three carbon atoms that can be saturated or unsaturated, unsubstituted or substituted.

Further preferred of the class of novel compounds hereof as represented above by Formulas (I) and (II), Group A is preferably selected from a grouping that has a glycerol backbone wherein one oxygen atom is linked to the linker of the above representative compounds; other hetero atoms attached to the glycerol backbone are linked: one, either oxygen, nitrogen or sulfur, to an alkyl or a fatty acid chain, and one, an oxygen, via a phosphodiester or other suitable linkage with a polar group, for example, choline. The fatty acid chain can be a saturated or unsaturated chain that will correspond with the substrate specificity, if any, of the specific hydrolyric enzyme in question.

In a second aspect, the present invention is directed to the method and means for treating a pathological disease state or condition mediated by a specific hydrolyric enzyme activity comprising administering to a subject susceptible to or experiencing said pathological disease state or condition an amount of novel hydrolytic enzyme inhibitor (inactivator) prodrug hereof, sufficient to irreversibly inactivate or inhibit said hydrolytic enzyme activity, and impart additional therapeutic effect, said hydrolytic enzyme inhibitor (inactivator) prodrug being administered in a pharmaceutically acceptable form.

The present invention as defined above in its various aspects includes all associated means and methods in the form of pharmaceutical embodiments, such as formulations and methods for preparing them, pharmaceutical uses, and so forth.

The present invention is described mechanistically in the manner it is presumed to biologically function: however, it shall be understood that the mechanism as such is not necessarily included within the ambit hereof should it actually differ in detail from that proposed. Following the presumed mechanism the functional residue "is"

CYC

That is, the method of treatment hereof has the endpoint of inhibition and/or inactivation of enzyme activity and additional therapeutic effect attributable to the liberated physiologically bioactive moiety attending the mechanistic action, regardless of the precise mechanism by which such endpoint is manifested in employing the compounds hereof.

DETAILED DESCRIPTION OF THE INVENTION

All documents referred to herein are hereby expressly incorporated by reference.

The present invention is illustrated by means of a model system whereby particular novel hydrolytic enzyme inhibitors (inactivators) hereof are used in connection with phospholipase $A_2$. The approach of this invention, as illustrated herein by the model system, can be and is generalized to facilitate the development of various other specific hydrolytic enzyme inhibitors hereof, in assays or treatment regimes for other specific hydrolytic enzymes. Included among such other hydrolyric enzymes are phospholipases, lipases, esterases, proteases, etc. Therapeutic applications for inhibitors hereof for these classes of enzymes arise from conditions such as inflammation, hypertension, lipid metabolism, obesity, etc.

The essential feature of the compounds hereof is the employment of a bifunctional link to join in a molecular ensemble functionally comprising the necessary structural features required for recognition by a specific hydrolytic enzyme active site(s) and a physiologically acceptable and physiologically bioactive leaving group. In preferred embodiments, the link is a dibasic acid capable of forming a cyclic anhydride. Upon enzymatic hydrolysis of the bond joining the link to the moiety conveying enzymatic specificity, the carboxylate anion of the resulting hydrolysis product is thought to act as a nucleophilic catalyst to cleave the ester bond joining the leaving group and the link, generating a cyclic anhydride. The reactivity of the anhydride with the active site of the enzyme creates a covalent bond between the two thus inactivating, or at least inhibiting, enzymatic activity. The reactivity of the anhydride is sufficiently great that if it should diffuse out of the active site of the enzyme, the overwhelming probability is that it would react with water before encountering another protein.

Thus, mechanistically, upon enzymatic hydrolysis of the bond joining the ].ink to the ensemble conveying enzymatic specificity, the carboxylate anion of the resulting hydrolysis product is thought to act as a nucleophilic catalyst to cleave the bond joining the leaving group and the link. The net result is to generate a reactive cyclic anhydride at the catalytically active site. Acylation by the anhydride of a nucleophilic group of the enzyme irreversibly inactivates the enzyme. The rate of formation of the anhydride can be modulated by adjustment of the pKa of the leaving group, and introduction of alkyl or other substituents on the intervening atoms of the link, or 3) incorporation of the intervening linker atoms into a cyclic structure such as an aromatic grouping.

The starting materials bearing such linkers or for constructing such linkers are available in the art —see, e.g., the Aldrich Chemical Co. More detail concerning the chemistry is set forth infra.

The principal advantages for the novel compounds of this invention are general applicability to hydrolytic enzymes and high specificity for particular target enzymes due to 1) compound design and 2) in one embodiment, occurrence of enzymatic acylation principally within the enzyme substrate complex that generated the cyclic compound.

The equivalent mechanistic principles apply where the link is a carbonyl/amide.

In the design of a moiety A that is specific for a given hydrolytic enzyme, advantage is taken of knowledge of the substrate specificity of the given hydrolytic enzyme. Examples of such can be taken from extant literature and include chymotrypsin, lipase, proteases and phospholipase $A_2$. More detail is provided infra.

Proteases can be subdivided into four major classes reflecting the nature of the catalytic site. Two classes promote hydrolysis of peptide bonds by nucleophilic catalysis entailing the formation of an acyl enzyme intermediate. These are the serine and cysteine proteases which utilize respectively either the hydroxyl of a serine residue or the thiol of a cysteine residue at the active site to cleave the peptide bond of the substrate. These enzymes will process nonpeptide bonds and accordingly chromogenic assays have been devised. Similarly, this substrate flexibility has allowed a variety of mechanism-based inhibitors to be developed.

The remaining two classes utilize an activated water molecule bound at the active site to cleave a peptide bond. Normally only peptide bonds are processed; consequently, chromogenic assays entailing the release of a dye as a function of enzyme activity have not been as feasible. The two classes are metallo-proteases and aspartic proteases. Good mechanism-based inhibitors for these two classes are unknown reflecting the rigorous criteria for substrate recognition.

In general, the active site of all proteases can be envisaged as lying in a cleft which may have a number of binding pockets to accommodate not only the side chain residues of the amino acid residue that comprise the peptide linkage to be cleaved but also the side chains of the amino acid residues that precede and follow the peptide bond to be cleaved. The high substrate specificity is a reflection not only of the binding requirements in the vicinity of the active site but also of these additional binding sites. Sites that bind to side chain residues that lie toward the N-terminus of the substrate are labeled $s_1-s_n$ proceeding away from the active site; similarly, sites that bind residues extending toward the C-terminus are labeled $s_1'-s_n'$. Proteases can either be exopeptidase (cleaves the first or last peptide bond of the substrate) or endopeptidases (cleaves a peptide bond embedded in the substrate).

To modulate the activity of proteases, the inhibitor must contain appropriate functionality such that "A" occupies the necessary $s_1'-s_n'$ recognition. "Y" and "B" would occupy the $s_1$ site. Some endopeptidases require occupancy of the $s_2$ and $s_3$ sites. In these cases the structure of "Y" must include features which would meet these requirements for substrate recognition. This is most easily accomplished by Y being a substituted aspartic or glutamic acid.

The following is a partial listing of therapeutically useful targets by enzyme class.

Metallo-proteases
 1) Collagenase, arthritis
 2) Elastase, emphysema, inflammation
 3) Angiotensin converting enzyme, hypertension
Aspartic proteases
 1) HIV protease, AIDS proliferation
 2) Renin, hypertension
 3) pepsin, ulcer
Cysteine Proteases
 1) Cathepsin B, inflammation
Serine Proteases
 1) Trypsin, pancreatitis
 2) Granulocyte elastase, inflammation
 3) Thrombin, coronary infarction For each of the above enzymes, the design of suicide inhibitors would be guided by known substrate requirements, and secondly, if available, X-ray structural data. For example, renin recognizes the sequence HisProPheHisLeuValIleHis and cleaves the Leu-Val bond. Replacement of the Leu residue with an aspartic acid residue in which the terminal carboxyl group was esterified with a leaving group "B" would generate a substrate that upon processing would generate a cyclic anhydride which upon acylation of renin could render it inactive. See Barrett & Salvesen Ed. *Proteinase Inhibitors* Vol. 12 Elsevier, Amsterdam (1986) and *Hydrolytic Enzymes* Ed. Neuberger & Brocklehurst, Elsevier, Amsterdam (1987).

The chemistry of preparing the novel hydrolytic enzyme inhibitors (inactivators) and substrates hereof is generally known to the skilled organic chemist. For example, where one is employing a dibasic acid in preferred embodiments hereof, both moieties A and B can be attached via usual esterification reactions. The dibasic acid starting material is either known in the art or can be prepared by standard dibasic acidification procedures. See standard organic chemistry and procedure texts.

Given the modular nature of the

ensemble, the synthetic sequence can be either: 1) reaction of the AXH with an activated dibasic acid followed by activation and reaction with BXH, or 2) synthesis of

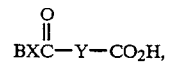

utilizing the procedure of Gaetjens et al., *J. Amer. Chem. Soc.* 82, 5328 (1960), for example, followed by activation and reaction with AXH.

A typical reaction pathway could include heating a mixture of a lysophospholipid, e.g., 1-decanoyl-sn-glycerol-3-phosphorylcholine with an excess of an anhydride, e.g., 2,2-dimethylglutaric anhydride in methylene dichloride in the presence of a base, e.g., triethylamine. After purification of the product half-acid phospholipid on silica gel, this product would be activated by reaction with an excess of an activator, e.g., oxalyl chloride, in methylene dichloride to produce an acid chloride. This would be subsequently reacted with an excess of the desired BXH group, e.g., p-nitrophenol, as an example where its cleavage could be followed spectrophotometrically and base, e.g., triethylamine. The product in methylene dichloride would then be purified. Alternatively, the BXH group, e.g., p-nitrophenol, could be mixed with an equivalent of base, e.g., sodium hydroxide, and allowed to react with an equivalent of the desired anhydride, e.g., 2,2-dimethylglutaric acid to produce the half-acid. This product can in turn be activated, e.g., with oxalylchloride, and reacted with a lyso phospholipid, e.g., 1-decanoyl-sn-glycerol-3-phosphorylcholine, to produce the desired final product.

Where the novel compounds hereof are selected from those wherein R is NH and/or each X is sulfur or NH, again, standard organic chemistry reactions apply.

Briefly, where R is NH, for an example, hydrogen chloride can be bubbled through a methylene chloride solution containing a equimolar mixture of 4-cyanobutyric acid and p-nitrophenol to generate the imino ether. Treatment of this compound with oxalyl chloride in methylene chloride followed by removal of the oxalyl chloride under vacuum and then by addition of moiety AXH and one equivalent of base generates the desired compound.

Where either X is sulfur or nitrogen, the same procedure as described infra for the X=oxygen compounds would be followed except for the substitution of the appropriate ASH or $ANH_2$ for AOH or BSH or $BNH_2$ for BOH.

Having described the particular model system employed in the present research for providing the generic class of prodrugs hereof, and having supplied the methodology for preparing such based upon generally well known organic chemistry reactions, and having illustrated a system whereby this model system can be employed in the case of Phospholipase $A_2$, and having supplied information useful to prepare pharmaceutically acceptable compositions of such compounds for use in the treatment of implicated disease states or conditions, the present disclosure is sufficient to enable one to prepare other prodrugs, methods of treatment and kits, etc., for their employment in an equivalent pharmaceutically based regimen. Thus, researchers using extant literature and techniques and the present concept shall well enough know how to prepare and design inhibitors (inactivators) of the present invention for specific hydrolytic enzymes either known or yet to be discovered. Thus, one would 1) vary the structural features of the natural substrate to identify the basic requirements, 2) synthesize a compound containing these features (embodied in moiety A), 3) covalently join A and Y (the link), and 4) attach B to the basic AY ensemble.

DETAILED DESCRIPTION

1. Definitions

By the terms relating to the linker depicted above by Y in the above formulas, is meant a moiety that serves two functions: It has at each end appropriate functionality so as to be capable of linkage with moieties A and B. In further preferred embodiments, that linkage is via carboxylate functionality. The second requirement is that it contain structural, steric features that favor formation of a cyclic compound upon enzymatic cleavage of the side grouping A and concomitant expulsion of B. In further preferred embodiments, the linker would contain at least two or three carbon atoms, saturated or unsaturated, substituted or unsubstituted. It may be a part of an aromatic arrangement such as is illustrated by a phenyl or naphthalene grouping. The only limitations foreseen are that upon cleavage of side groupings A and B, in situ chemically proximate to the target enzyme, it would intramolecularly bond so as to form a cyclic compound. In the case of the preferred embodiment, the end cyclic compound would be an anhydride (see FIG. 1, for example).

By the term referring to a moiety capable of binding to an active site is meant an active site specific moiety that is recognizable by a particular hydrolytic enzyme. In the case of lipases, such a moiety could contain a glycerol backbone where one of the oxygen atoms is linked to the linker and the other two oxygens would be linked to a saturated or unsaturated acyl or alkyl chain appropriate to the enzyme in question. In the case of phospholipase hydrolyric enzymes, one of the two other oxygen atoms would be linked to a phosphodiester having a polar group, for example, choline, ethanolamine, serine, inositol, glycerol, methyl, etc. In the case of other esterases that act on lipids, such as cholesterol esterase, the moiety could contain cholesterol or a derivative.

In the case of proteases, the moiety capable of binding to an active site could be composed of an appropriate amino acid peptide, or analogue, depending on the substrate requirements of the particular enzyme. For some proteases certain substituents on the linker Y and the leaving group (BX) which may also be an amino acid, peptide or analogue thereof, are also appropriate.

In the case of terms relating to moiety B, there are the requirements: 1) that it be a component of a good leaving group; 2) that, to be used in drug applications where it is a concomitant enzyme inhibitor, the reaction attending intramolecular cyclization of the functional residue be generally rapid relative to diffusion and that it be a component of a physiologically acceptable leaving group; and 3) that it itself by physiologically bioactive.

By the term "modulating" in respect of various disease states or conditions is meant affecting the hydrolytic enzyme activity where such activity is implicated in the onset or continuance or propensity for given disease state or condition symptoms. In the case of preferred embodiments herein, various inflammatory conditions can be alleviated by use of a phospholipase $A_2$ inhibitor of the present invention so as to reduce or limit the action of said enzyme in the production of products or co-products that either themselves, or after further reactions, induce inflammatory states.

In therapeutic applications, it is essential that the compounds hereof be non-toxic or physiologically acceptable. In particular, the characterization of leaving group BX or its component B, must satisfy this criterion, as a distinct departure from its characterization when used in assay applications where it need only be detectable and measurable. Further, in the prodrugs hereof, the B containing leaving group is also physiologically bioactive. Examples of physiologically acceptable, bioactive leaving groups are: Substituted or unsubstituted cycloaliphatic or unsaturated (including aromatic) cyclic alcohols, thiols, or imides, such as p-sulfophenyloxy, p-trifluoromethylphenyloxy, p-hydroxytetrafluorophenyloxy, p-halophenyloxy, o,o,p-trimethylphenyloxy, p-acetyloxyphenyloxy, p-(tritrifluoromethyl)methylphenyloxy, p-trimethylaminophnyloxy, p-cyanophenyloxy, o-carboxyphenyloxy, o-carboxy-p-aminophenyloxy, N(acetylamino)phenyloxy, 2-(1-carboxyeth-1-yl)-napth-6-yl-oxy, and so forth.

See also, for example, Kirby, *Adv. Phys. Org. Chem.* 17, 183–278 (1980). Physiological acceptability can be determined as well in accord with federally regulated clinical studies.

By "lower alkyl" or "alkyl" is meant all isomers comprising 1 to 4 carbon atoms, inclusive.

2 Examples

Preparation of Model Phospholipase $A_2$ Specific Inhibitor Prodruqs

Material

All lysophospholipids, 1,2-dipalmitoyl-sn-glycero-3-phosphorylcholine (DPPC), an d 1,2-dicaproyl-snglycero-3-phosphorycholine (DCPC) are purchased commercially. All cyclic an hydrides except 2,2-dimethylsuccinic anhydride are obtainable from Aldrich Chemical Co. The latter is prepared by treating dimethyl-succinic acid (Aldrich) with a 3-fold excess of trifluoroacetic anhydride in $CH_2Cl_2$ for 2 hours, removing the volatiles, and using the residual solid without further purification. All solvents and reagents are of reagent quality.

$PLA_2$ obtained from cobra venom (*N. naja naja*) was purified as described in Hazlett et al., *Toxicon* 23, 57 (1985).

Preparation of Physiologically Acceptable, Bioactive SIBLINKS

To 42 mg (0.1 mmol) of 1-decanoyl-sn-glycerol-3-phosphorylcholine in 3 ml of $CH_2Cl_2$ is added 60 mg (0.43 mmol) of 2,2-dimethylglutaric anhydride followed by 50 μl (0.35 mmol) of $Et_3N$. The reaction is heated for 24 hours at 45° C. If the reaction is not complete by TLC analysis (1:10:22 $H_2O$/MeOH/$CHCl_3$ using Analtech Silica Gel G-250 glass plates with UV indicator visualized with molybdate spray), an additional 30 mg (0.21 mmol) of anhydride with 40 μl (0.28 mmol) of $Et_3N$ are added and the reaction heated for an additional 10 hours until all starting lipid is consumed. After removal of all volatile components, the residue is leached three to four times with 10-ml portions of dry $Et_2O$ to remove unreacted anhydride and triethylamine glutaric acid salts. The remaining crude half-acid phospholipid after evacuation at 0.1 tort is converted to the acid chloride upon treatment with 2 ml of $CH_2Cl_2$ containing 0.3 ml of oxalyl chloride for 5 hours at 20° C. Alternatively the half-acid phospholipid is isolated by washing with 0.1N HCl the crude acylation product dissolved in 2:1 $CHCl_3$/MeOH. Pure half-acid phospholipid is obtained after chromatography on silica gel using 1:4:30:65 HOAc/$H_2O$/MeOH/$CHCl_3$ as the eluant.

The acid chloride is separated from oxalyl chloride by removal of the volatiles in vacuo followed by two cycles of dissolution in 2 ml of dry benzene and evaporation. A solution of 65 mg (0.43 mmol) of p-(N-acetylamino)-phenol and 60 μl (0.42 mmol) of $Et_3N$ in 4 ml of $CH_2Cl_2$ is added to a 1-ml $CH_2Cl_2$ solution of the acid chloride. If necessary, additional phenol and amine are added to ensure that an excess of p-(N-acetylamino)-phenoxide is present. After standing overnight at 20° C., the volatiles are removed and the residue taken up in 5 ml of 2:1 $CHCl_3$/MeOH and washed with 4 ml of 0.1 N HCl. The solvent is removed, and the residue containing phospholipids is chromatographed on silica gel using 10–33% MeOH/$CHCl_3$ as the eluant to give the desired phospholipid.

Pure samples are obtained after HPLC chromatography using anhydrous MeOH to elute the lipid from a Brownlee $C_{18}$ column.

Other compounds falling within the scope of the present invention are prepared following analogous procedures with appropriate starting compounds as set forth in the following Table:

TABLE I

| | Starting Compounds | |
|---|---|---|
| For B Moiety | For Y Moiety | For A Moiety |
| salicyclic acid | glutaric anhydride | 1-decanoyl-lyso-PC* |
| salicyclic acid | glutaric anhydride | 1-decanoyl-lyso PE (phosphatidyl-ethanolamine) |
| salicyclic acid | glutaric anhydride | 1-decanoyl-lyso PG (phosphatidyl-glycerol) |
| salicyclic acid | glutaric anhydride | 1-decanoyl-lyso PS (phosphatidyl-serine) |
| p-(N-acetylamino)phenol | pimelic anhydride | 1-decanoyl-lyso PC |
| p-(N-acetylamino)phenol | pimelic anhydride | 1-decanylthio-lyso PC |
| p-(N-acetylamino)phenol | 2-methylsuccinic anhydride | 1-decanylthio-lyso PG |
| p-(N-acetylamino)phenol | 2,2-dimethylsuccinic anhydride | 1-decanylthio-lyso PE |
| p-(N-acetylamino)phenol | 1,2-dimethylsuccinic anhydride | 1-decanylthio-lyso PS |
| p-trifluoromethyl phenol | maleic anhydride | 1-decanoyl-lyso-PC |
| p-trifluoro-methyl phenol | norbornyl anhydride | 1-decanoyl-lyso-PC |
| p-bromo phenol | norbornyl anhydride | 1-decanoyl-lyso-PC |
| p-acetyloxy phenol | glutaric anhydride | 1-decanoyl-lyso-PC |
| 2-(6-hydroxynaph-2-yl)propionic acid | glutaric anhydride | 1-decanoyl-lyso-PC |
| indomethacin | naphthylene-2,8-dicarboxylic acid anhydride | 1-decanoyl-lyso-PS |
| tolmetinsodium | benzene-1,2-dicarboylic acid anhydride | 1-hexanoyl-lyso PC |
| salicylic acid | benzene-1,2-dicarboylic acid anhydride | 1-hexanoyl-lyso PC |

*1-decanoyl-2-lysophosphatidylcholine (full name 1-decanoyl-sn-glycero-3-phosphorylcholine)

Preincubation Conditions

SIBLINKS hereof are purified by HPLC SIBLINKS vesicles are prepared by sonicating 2–4 mg of phospholipid in 1 ml of 100 mM KCl using four 30-s pulses of a MSE 100-watt sonicator. The resulting solution is centrifuged (25 min. at 9,500×g, 4° C.). The vesicles after separation from the pellet are analyzed for free BX leaving group. To minimize slow hydrolysis of the aryl ester, the vesicles are stored at 4° C. Further purification of the above vesicle preparation by ultracentrifugation (4 hours at 50,000×g, 4° C.) does not significantly alter inhibition time courses.

Standard preincubation conditions utilizes 100 μM SIBLINKS as sonicated vesicles with $PLA_2$ in 20 mM Tris-HCl (pH 8.0), 10 mM $CaCl_2$, and 100 mM KCl at 20° C. The same conditions are used for preincubation with mixed micelles except for the presence of TRITON X-100 ®. As used herein, TRITon X-100 (Rohm-Haas) is an octoxynol as defined by

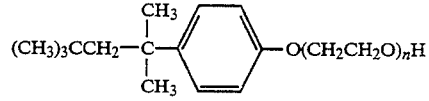

The concentration of *N. naja naja* $PLA_2$ is 0.37 μM (5 μg/ml). The preincubation concentrations of the $PLA_2$s from other sources ranges from 5 to 20 μg/ml.

Residual Activity Determination

To determine the amount of residual enzyme activity remaining after preincubation, a titrametric assay is employed in which 5–20 μl of the preincubation solution is added to 1.7 ml of the substrate solution containing 10 mM CaCl$_2$ at 40° C. Thus, the preincubation mixture is diluted so activity toward residual SIBLINKS is negligible, and activity toward added substrate is maximized. PLA$_2$s obtained from *N. naja naja* and bee venoms are routinely assayed with 5 mM DPPC in mixed micelles with 20 mM TRITON X-100 ®. The assay utilizes 50 ng of protein. Deems et al., *Methods Enzymology* 703 (1981). Porcine pancreatic PLA$_2$ is assayed titrametrically with 100 ng of protein/assay and an egg lecithin/sodium deoxycholate mixture as substrate. Nieuwenhuizen et al., *Methods Enzymology* 32b, 147 (1974). *C. Adamanteus* and *C. atrox* PLA$_2$s are assayed titrametrically using 70 ng of protein/assay with the same DPPC/TRITON X-100 ® assay described above for *N. naja naja* except for the addition of 1 mg/ml of bovine serum albumin. Pluckthun et al., *J. Biol. Chem.* 260, 11099 (1985). Residual activities (percent) are calculated from the mole of base consumed titrametrically relative to a PLA$_2$ solution preincubated under the same conditions in the absence of the SIBLINKS.

SIBLINKS Inhibition

The reaction is simultaneously monitored during preincubation of PLA$_2$ with SIBLINKS vesicles. Titrametric assays, as described above, reveals the amount of residual enzymatic activity from which the number of mole of PLA$_2$ inactivated can be calculated. To ascertain maximum inhibition, preincubations are continued for 24 hours or less if no further loss of activity with time occurs within experimental error. The partition ratio (P) of the number of mole of SIBLINKS hydrolyzed per mole of enzyme inactivated is calculated using independent determinations of mole of B leaving group released and mol of PLA$_2$inactivated. P values are calculated several times during the time course of inactivation studies. P is essentially constant between 20 and 70% inactivation. The value of P for a specific SIBLINKS is an average of the three or four values measured during the determination of each inactivation time course.

Cyclic Anhydride Inhibition

The following procedure is utilized to measure PLA$_2$inhibition by cyclic anhydrides. A CH$_2$Cl$_2$ solution of the anhydride is evaporated under an N$_2$ stream. Immediately, 400 μl of the appropriate PLA$_2$ in 20 mM Tris-HCl (pH 8.0), 10 mM CaCl$_2$, and 100 mM KCl at 20° C. is added followed by vortexing to ensure rapid mixing. Aliquots are assayed titrametrically after 5 min; no further change in activity is observed after an additional 1–2 hours.

Preparative Scale Inhibition of PLA$_2$

When large amounts of PLA$_2$ inhibited by cyclic anhydride are needed, the following procedure is employed. To 0.5–0.9 ml of buffer (0.7 M Tris-HCl. pH 8.0) containing 0.15–0.2 mg of PLA$_2$ is added 6.5–9 mg of cyclic anhydride 26. After vortexing and standing for 1 hour, a second portion of anhydride is added to ensure that maximum inhibition was obtained. The suspension is applied to a Pharmacia LKB Biotechnology Inc. G-25 PD-10 column that was preequilibrated with buffer (10 mM K$_2$HPO$^1$, pH 8), and the protein is eluted with the same buffer. Similar conditions are employed to obtain PLA$_2$ inhibited by SIBLINKS except for a 20 hour preincubation with 500 μM SIBLINKS vesicles and the inclusion of 10 mM CaCl$_2$ and 100 mM NaCl. The 0.5 ml chromatographic fractions are analyzed for protein and B leaving group ester; only protein fractions free of the SIBLINKS are utilized.

Hydroxylamine Studies

The following procedure is employed for hydroxylamine treatment. The appropriate amount of a freshly prepared stock solution of 50 mM NH$_2$OH HCl in 1M Tris-HCl (pH 8.0) is added to the PLA$_2$ solution to a final concentration of 5 mM. After vortexing and before assaying titrametrically for PLA$_2$ activity, the solution is allowed to stand 1–2 hours at 20° C. This reaction is performed in a closed vial to minimize NH$_2$OH oxidation.

Assays

All assays may be measured in 0.4 ml buffer (10 mM Tris-HCl, pH8, 10 mM CaCl$_2$, and 100 mM KCl).

One may plot specific activity for 20 ng phospholipase A$_2$ obtained from cobra venom (Naja naja naja) as a function of the concentration of SIBLINKS hereof in 3.2:1 mixed micelles of Triton X-I00 and phospholipid at 40° C. See Dennis, *J. Lipid Research* 14, 152 (1973) and Deems and Dennis, *Methods in Enzymology* 71, 703 (1981).

One may plot initial velocities (expressed at Δ O.D. at λ=400 nm in 20 sec.) observed with phospholipase A$_2$ (specific activity 1470 Mmol min$^{-1}$mg$<^1$ which is linear with protein concentration from 0.5 ng to 100 ng using 1.8:1 using Triton/phospholipid mixed micelles at 40° C. containing 0.4 mM of SIBLINKS compound.

The hydrolysis reaction rate is a function of the ratio of mole fraction of substrate in the Triton/phospholipid mixed micelle; the rate diminishes three-fold as the surface ratio increases from 1.6:1 to 3:1 to 4.5:1 to 7:1. Unilamellar vesicles (SUVs) prepared by sonication of prodrug compound followed by centrifugation, are readily hydrolyzed by phospholipase A$_2$; for a 400 μM solution of SUV's, V was 265 μmol/min/mg as compared to 550 measured for 400 μM of compound 1a in 3.2:1 Triton mixed micelles.

The time courses for inactivation of phospholipase A$_2$obtained from cobra venom by preincubation of prodrugs hereof are obtained by 1) preincubate a 260:1 mixture of inhibitor 1 to PLA$_2$ in 1 ml solution containing 5 μg/ml of PLA$_2$, 100 μM vesicles of prodrug 1a-1e, 20 mM Tris-HCl pH 8, 10 mM CaCl$_2$ and 0.1M KCl at 20° C., 2) measure titrimetrically the hydrolysis rate initiated by addition of a 20 μl aliquot of the above solution to 1.7 ml of 40° C. assay medium containing 5 mM 1,2-dipalmitoyl phosphatidylcholine, 10 mM CaCl$_2$ and 20 mM Triton X-100.

The reader is directed to literature extant that supply relevant details as to specific, assays in measuring activity herein, and to devising pharmaceutically acceptable compositions and methodology for the efficacious treatment of disease states, having supplied herein the essence of the present invention for essentially participating in such clinical endeavors. For example, see U.S. Pat. Nos. 4826958, 4833152, 4616089, 4788304, 4447445, and WO86/06100 (Oct. 23, 1986).

Drug entities prepared as described above for specific target hydrolytic enzyme inhibition and/or inactivation are compounded in accord with known techniques to produce useful pharmaceutical compositions that are pharmaceutically acceptable for appropriate administration in the treatment of pathological conditions or disease states manifested etiologically by such hydrolytic enzyme activity.

Such drugs are tested for safety, dose response and efficacy in humans as per federal regulations. Ordinary studies conducted pursuant to those regulations shall determine the safety and efficacious dose regimens appropriate in the circumstances for the treatment of the particular disease state of concern. The attendant clinical studies are in the area of routine experimentation generally within the ken of the art-skilled. These drugs are administered via standard formulations to patients with such disease states, again either topically, orally, parenterally, rectally, alone or in combination, at regular intervals or as a single bolus, or as a continuous infusion, and so forth.

For example, a typical pharmaceutical composition containing the active compound hereof together with an appropriate pharmaceutically acceptable carrier entity(ies) may be in the range of about 0.1 mg to about 500 mg per dose, or about 1 microgram to about 7 mg per kilogram of body weight. Such amount would be considered "an amount sufficient to inactivate or inhibit the activity of a given hydrolytic enzyme". Again, the end-point of such administration would be the inhibition or inactivation of the given hydrolytic enzyme manifested by an alleviation of the symptoms associated with the disease. The regulatory protocols necessary to produce marketable drug entities provide the exact dosage and the details of the "pharmaceutically acceptable form" of a compound of this invention.

The information contained in the part hereof supra entitled "Assays" are materials and methods and results of in vitro studies using certain of the compounds hereof as models for the testing of inhibition and/or inactivation of a particular model hydrolytic enzyme. These protocols and results are believed to be translatable within the routine experiment of the art-skilled to related enzymes of human origin, and into an animal, and hence, a human being. As mentioned above, confirmation of such translation into these in vivo systems would be readily measurable by the end point of the mechanism believed operative for the compounds of the present invention that are physiologically acceptable. Thus, in such an in vivo system, if the organism exhibits alleviation of symptoms associated with a given disease state that is known to be linked to a particular hydrolytic enzyme against which the test compound hereof is effected, then activity in such a biosystem with such test compound can be presumed in line with and consequential to the corresponding in vitro tests, as provided above.

The foregoing description details specific methods that can be employed to practice the present invention. Having detailed specific methods initially used to characterize, prepare and use the inhibitors (inactivators) and substrates hereof, and further disclosure as to specific model systems, those skilled in the art will well enough know how to devise alternative reliable methods for arriving at the same information and for extending this information to other hydrolytic enzyme systems. Thus, however detailed the foregoing may appear in text, it should not be construed as limiting the overall scope hereof; rather, the ambit of the present invention is to be governed only by the lawful construction of the appended claims.

What is claimed is:

1. A method of inactivating or inhibiting a phospholipase A enzyme, comprising administering to a subject susceptible to or experiencing a condition mediated by the activity of said enzyme an amount sufficient to inactivate or inhibit the activity of said enzyme of a pharmaceutically acceptable form of a compound of the formula:

wherein
R is oxygen or imino,
  each X independently is oxygen, sulfur or imino,
A is a moiety recognized by a phospholipase A enzyme such that said enzyme hydrolyses the bond linking AX with C(0)Y,
B. is a physiologically bioactive leaving group,
Y is an alkylene or alkenylene or alkylene or alkenylene substituted with one or more lower alkyl groups.

2. The method according to claim 1 wherein, in said compound, AX is a radical of 1-decanoyl-sn-glycerol-3-phosphorlycholine.

3. The method according to claim 2 wherein, in said compound, Y is a radical of n-propylene.

4. The method according to claim 2 wherein, in said compound, Y is a radical of 1,1-dimethyl-n-propylene.

5. The method according to claim 2 wherein, in said compound, Y is a radical of 2,2-dimethyl-n-propylene.

6. The method according to claim 2 wherein, in said compound, Y is a radical of ethylene.

7. The method according to claim 2 wherein, in said compound, Y is a radical of 1,1-dimethylethylene.

8. The method according to claim 2 wherein, in said compound XB is a radical of p-(N-acetylamino)-phenyloxy.

9. The method according to claim 2 wherein, in said compound, XB is a radical of o-carboxyphenyloxy.

10. A compound of the formula:

wherein
R is oxygen or imino,
  each X independently is oxygen, sulfur or imino,
A is a moiety recognized by a phospholipase A enzyme such that said enzyme hydrolyses the bond linking AX with C(0)Y,
B is a physiologically bioactive leaving group,
Y is an alkylene or alkenylene or alkylene or alkenylene substituted with one or more lower alkyl groups.

11. A compound according to claim 10 wherein XB is a radical of a compound of a class selected from cycloaliphatic and unsaturated cyclic alcohols, thiols or imides.

12. A compound according to claim 11 wherein XB is o-carboxyphenyloxy.

13. A compound according to claim 12 wherein AX is a radical of 1-decanoyl-sn-glycero-3-phosphorylcholine.

14. A compound according to claim 13 wherein R is oxygen and Y is n-propylene.

15. A compound according to claim 13 wherein R is oxygen and Y is 1,1-dimethyl-n-propylene.

16. A compound according to claim 13 wherein R is oxygen and Y is 2,2-dimethyl-n-propylene.

17. A compound according to claim 13 wherein R is an oxygen atom and Y is ethylene.

18. A compound according to claim 13 wherein R is oxygen and Y is 1,1-dimethylethylene.

19. A compound according to claim 10 wherein R is oxygen and Y is 1,1-dimethylethylene.

20. A compound according to claim 19 wherein AX is a radical of 1-decanoyl-sn-glycerol-3-phosphorylcholine.

21. A compound according to claim 20 wherein X in XB is oxygen.

22. A compound according to claim 20 where XB is o-carboxyphenyloxy.

23. A compound according to claim 20 wherein XB is p-(N-acetylamino)-phenyloxy.

24. A compound according to claim 20 wherein XB is 2-(1-carboxyeth-1-yl)-naph-6-yloxy.

25. A compound according to claim 20 wherein XB is o-carboxy-p-aminophenyloxy.

* * * * *

UNITED STATES PATENT AND TRADEMARK OFFICE
CERTIFICATE OF CORRECTION

PATENT NO. : 5,352,673
DATED : October 4, 1994
INVENTOR(S) : Dennis

It is certified that error appears in the above-indentified patent and that said Letters Patent is hereby corrected as shown below:

<u>ON THE COVERSHEET</u>  Item [56]

In column 2, lines 2-3 of the coversheet delete "Gaetjens et al, Journal of the American Chemical Society, 42: 5328, 1960."

In column 2, line 7 of the coversheet, after "0772-0777", delete "Rbeles" and replace with --Abeles--.

In column 2 of the coversheet, line 8, delete "Edwards et al" and replace with --Washburn, W.N. et al--.

In column 2 of the coversheet, line 10, delete "112:2042" and replace with --112:2040-2041--.

In column 4, line 42, delete "].ink" and replace with --link--.

In column 4, line 50, before "adjustment" insert --1) --.

In column 4, line 50, before "intro-" insert --2) --.

In column 9, line 11, delete "57" and replace with --457--.

UNITED STATES PATENT AND TRADEMARK OFFICE
CERTIFICATE OF CORRECTION

PATENT NO. : 5,352,673
DATED : October 4, 1994
INVENTOR(S) : Dennis

It is certified that error appears in the above-indentified patent and that said Letters Patent is hereby corrected as shown below:

In column 10, Table I, in the first column under the heading "For B Moiety", after the fourth occurrence of "p-(N--acetylamino)phenol" (approximately line 18.5), insert --p-(N-acetylamino)phenol--.

In column 10, Table I, in the second column under the heading "For Y Moiety" after "1,2-dimethylsuccinic anhydride" (approximately line 18.5), insert --3,3-dimethylsuccinic anhydride--.

In column 10, Table I, in the third column under the heading "For A Moiety" after "1-decanylthio-lyso PS" insert --1-decanylamino-lyso PC--.

In column 11, line 10, after "*Enzymology*" and before "703", insert -- 71,--.

In column 12, line 31, replace "$min^{-1}mg^{<1}$" with --$min^{-1}mg^{-1}$--.

UNITED STATES PATENT AND TRADEMARK OFFICE
CERTIFICATE OF CORRECTION

PATENT NO.  : 5,352,673
DATED       : October 4, 1994
INVENTOR(S) : Dennis

It is certified that error appears in the above-indentified patent and that said Letters Patent is hereby corrected as shown below:

<u>IN THE ABSTRACT</u>

In the last line of the Abstract, replace "effect" with --effects--.

In columns 9 and 10, replace each of the four occurrences in Table I of "salicyclic acid" with --salicylic acid--.

Signed and Sealed this

Twenty-sixth Day of September, 1995

Attest:

BRUCE LEHMAN

*Attesting Officer*      *Commissioner of Patents and Trademarks*